US009840276B2

United States Patent
Griffiths et al.

(10) Patent No.: US 9,840,276 B2
(45) Date of Patent: Dec. 12, 2017

(54) SURGICAL PATIENT SIDE CART WITH STEERING INTERFACE

(71) Applicant: INTUITIVE SURGICAL OPERATIONS, INC., Sunnyvale, CA (US)

(72) Inventors: Paul G. Griffiths, Santa Clara, CA (US); Paul W. Mohr, Mountain View, CA (US); Alan W. Petersen, Cupertino, CA (US); David Robinson, Mountain View, CA (US); Nitish Swarup, Sunnyvale, CA (US); Mark W. Zimmer, Fremont, CA (US); Alexander Makhlin, Chicago, IL (US); Julio Santos-Munne, Glenview, IL (US); Eric Faulring, Albuquerque, NM (US); Thomas Moyer, Salt Lake City, UT (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 15/463,740

(22) Filed: Mar. 20, 2017

(65) Prior Publication Data
US 2017/0253270 A1 Sep. 7, 2017

Related U.S. Application Data

(63) Continuation of application No. 15/073,811, filed on Mar. 18, 2016, now Pat. No. 9,623,902, which is a
(Continued)

(51) Int. Cl.
*B62D 6/10* (2006.01)
*B62D 1/12* (2006.01)
(Continued)

(52) U.S. Cl.
CPC ............... *B62D 6/10* (2013.01); *A61B 34/35* (2016.02); *A61B 50/10* (2016.02); *A61B 50/13* (2016.02);
(Continued)

(58) Field of Classification Search
CPC ........ B62D 6/10; B62D 1/12; A61B 19/0248; A61B 50/10; A61B 50/13
(Continued)

(56) References Cited

U.S. PATENT DOCUMENTS

| 5,746,282 A | 5/1998 | Fujiwara et al. |
| 5,810,104 A | 9/1998 | Campbell |

(Continued)

FOREIGN PATENT DOCUMENTS

| JP | H05286453 A | 11/1993 |
| JP | 2010008204 A | 1/2010 |

OTHER PUBLICATIONS

Extended European Search Report for Application No. 14770421.7, dated Sep. 15, 2016, 6 pages.
(Continued)

*Primary Examiner* — Yazan Soofi
(74) *Attorney, Agent, or Firm* — Jones Robb, PLLC

(57) ABSTRACT

A patient side cart for a teleoperated surgical system can include one or more wheels positioned to support the cart for wheeled motion on a ground surface, at least one manipulator portion for holding a surgical instrument, a steering interface having a grasping portion and comprising a sensor positioned to sense turning, fore, and aft forces exerted on the grasping portion to move the cart, wherein the sensor is in signal communication with a drive control system of the patient side cart, and an additional sensor operatively coupled to the drive control system. The additional sensor may be positioned between the steering interface and the
(Continued)

wheels on a side of the cart at which the steering interface is positioned, wherein in response to a force exerted on the additional sensor during backward motion of the cart in response to an aft force exerted on the grasping portion, the sensor sends a signal to the drive control system to stop motion of the cart.

20 Claims, 9 Drawing Sheets

Related U.S. Application Data continuation of application No. 14/208,663, filed on Mar. 13, 2014, now Pat. No. 9,308,937.

(60) Provisional application No. 61/791,924, filed on Mar. 15, 2013.

(51) Int. Cl.
*A61B 50/10* (2016.01)
*A61B 50/13* (2016.01)
*A61B 34/35* (2016.01)
*A61B 90/00* (2016.01)
*A61B 50/18* (2016.01)
*A61B 17/00* (2006.01)
*A61B 34/30* (2016.01)

(52) U.S. Cl.
CPC .............. *A61B 50/18* (2016.02); *B62D 1/12* (2013.01); *A61B 34/30* (2016.02); *A61B 2017/00482* (2013.01); *A61B 2050/185* (2016.02); *A61B 2090/064* (2016.02)

(58) Field of Classification Search
USPC ........................................................ 701/41
See application file for complete search history.

(56) References Cited

U.S. PATENT DOCUMENTS

| | | | |
|---|---|---|---|
| 6,220,379 B1 | 4/2001 | Schugt et al. | |
| 6,227,320 B1 | 5/2001 | Eggert et al. | |
| 6,276,471 B1 | 8/2001 | Kratzenberg et al. | |
| 6,285,742 B1 | 9/2001 | Haumann et al. | |
| 6,422,241 B1 | 7/2002 | Soukal | |
| 7,017,689 B2 | 3/2006 | Gilliland et al. | |
| 7,076,830 B2 | 7/2006 | Conner et al. | |
| 7,080,703 B2 | 7/2006 | David et al. | |
| 7,090,042 B2 | 8/2006 | Coveyou et al. | |
| 7,273,115 B2 | 9/2007 | Kummer et al. | |
| 7,318,309 B2* | 1/2008 | Osborne | A01D 34/6806 180/19.3 |
| 7,407,024 B2 | 8/2008 | Vogel et al. | |
| 7,530,412 B2 | 5/2009 | Heimbrock et al. | |
| 7,533,892 B2* | 5/2009 | Schena | B62D 1/14 180/19.1 |
| 7,562,729 B2 | 7/2009 | Hammerle et al. | |
| 7,661,493 B2 | 2/2010 | Rose | |
| 7,831,292 B2 | 11/2010 | Quaid et al. | |
| 7,845,441 B2 | 12/2010 | Chambers | |
| 7,909,122 B2 | 3/2011 | Schena et al. | |
| 9,101,348 B2 | 8/2015 | Griffiths et al. | |
| 9,308,937 B2 | 4/2016 | Griffiths et al. | |
| 9,623,902 B2 | 4/2017 | Griffiths et al. | |
| 2005/0247508 A1* | 11/2005 | Gilliland | B62B 5/06 180/402 |
| 2007/0041817 A1 | 2/2007 | Kakinuma | |
| 2008/0287963 A1 | 11/2008 | Rogers et al. | |
| 2010/0169815 A1* | 7/2010 | Zhao | B25J 9/1633 715/771 |
| 2010/0180380 A1 | 7/2010 | Van Scheppingen et al. | |
| 2010/0243924 A1 | 9/2010 | Uchida et al. | |
| 2011/0087238 A1* | 4/2011 | Wang | B25J 9/1689 606/130 |
| 2011/0264108 A1 | 10/2011 | Nowlin et al. | |
| 2014/0107665 A1* | 4/2014 | Shellenberger | A61B 34/30 606/130 |
| 2015/0066050 A1 | 3/2015 | Jardine et al. | |
| 2016/0022360 A1 | 1/2016 | Griffiths et al. | |

OTHER PUBLICATIONS

International Search Report and Written Opinion for Application No. PCT/US14/26153, dated Aug. 14, 2014, 16 pages.
International Search Report and Written Opinion for Application No. PCT/US14/26374, dated Jul. 24, 2014, 15 pages.
Machine Translation of JP 2010-008204A.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SURGICAL PATIENT SIDE CART WITH STEERING INTERFACE

This application is a continuation of U.S. patent application Ser. No. 15/073,811, filed Mar. 18, 2016, which is a continuation of U.S. patent application Ser. No. 14/208,663, filed Mar. 13, 2014 (now U.S. Pat. No. 9,308,937, which claims the benefit of U.S. Provisional Application No. 61/791,924, filed Mar. 15, 2013, each of which is incorporated by reference herein in its entirety.

TECHNICAL FIELD

Aspects of the present disclosure relate to a steering interface for a user to maneuver a cart, such as, for example, a teleoperated (robotic) surgical system patient side cart. Aspects of the present disclosure also relate to a replaceable steering interface for a cart.

INTRODUCTION

Some minimally invasive surgical techniques are performed remotely through the use of teleoperated (robotically-controlled) surgical instruments. In teleoperated (robotically-controlled) surgical systems, surgeons manipulate input devices at a surgeon console, and those inputs are passed to a patient side cart that interfaces with one or more teleoperated surgical instruments. Based on the surgeon's inputs at the surgeon console, the one or more teleoperated surgical instruments are actuated at the patient side cart to operate on the patient, thereby creating a master-slave control relationship between the surgeon console and the surgical instrument(s) at the patient side cart.

A patient side cart need not remain stationary in a particular location, such as within one operating room, but instead may be moved from one location to another. For example, a patient side cart may be moved from one location to another, such as from one location in an operating room to another location in the same operating room. In another example, a patient side cart may be moved from one operating room to another operating room.

One consideration in moving a patient side cart of a teleoperated surgical system is the ease with which the patient side cart may be moved by a user. Due to its weight, size, and overall configuration, it may be desirable to provide a patient side cart with a drive to assist a user with moving the patient side cart. Such a drive may be controlled based upon input from the user to move a patient side cart in a relatively easy manner. Further, it may be desirable to provide a patient side cart with controls to drive and move the patient side cart that are not complex but are instead relatively easy to use.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a patient side cart for a teleoperated surgical system may include at least one manipulator portion for holding a surgical instrument and a steering interface. The steering interface may include at least one sensor positioned to sense turning, fore, and aft forces exerted by a user to move the cart. The steering interface may further include a coupling mechanism to removably couple the steering interface with the patient side cart. The at least one sensor may be placed in signal communication with a drive control system of the patient side cart when the steering interface is in a coupled state with the patient side cart.

In accordance with another exemplary embodiment, a steering interface for a cart including a drive control system may include at least one sensor positioned to sense turning, fore, and aft forces exerted by a user to move the cart. A coupling mechanism may be included in the steering interface for removably coupling the steering interface with the patient side cart. At least one sensor may be configured to be placed in signal communication with the drive control system of the cart when the steering interface is in a coupled state with the cart.

In accordance with another exemplary embodiment, a method of moving a patient side cart of a teleoperated surgical system, the patient side cart including a steering interface and a surgical instrument, may include the step of detecting a force applied to the steering interface with a sensor of the steering interface. The method may include a step of providing a signal from the sensor to a drive system of the patient side cart. The method may include a step of driving at least one wheel of the patient side cart on a basis of the signal provided from the sensor of the steering interface.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Figure 1:
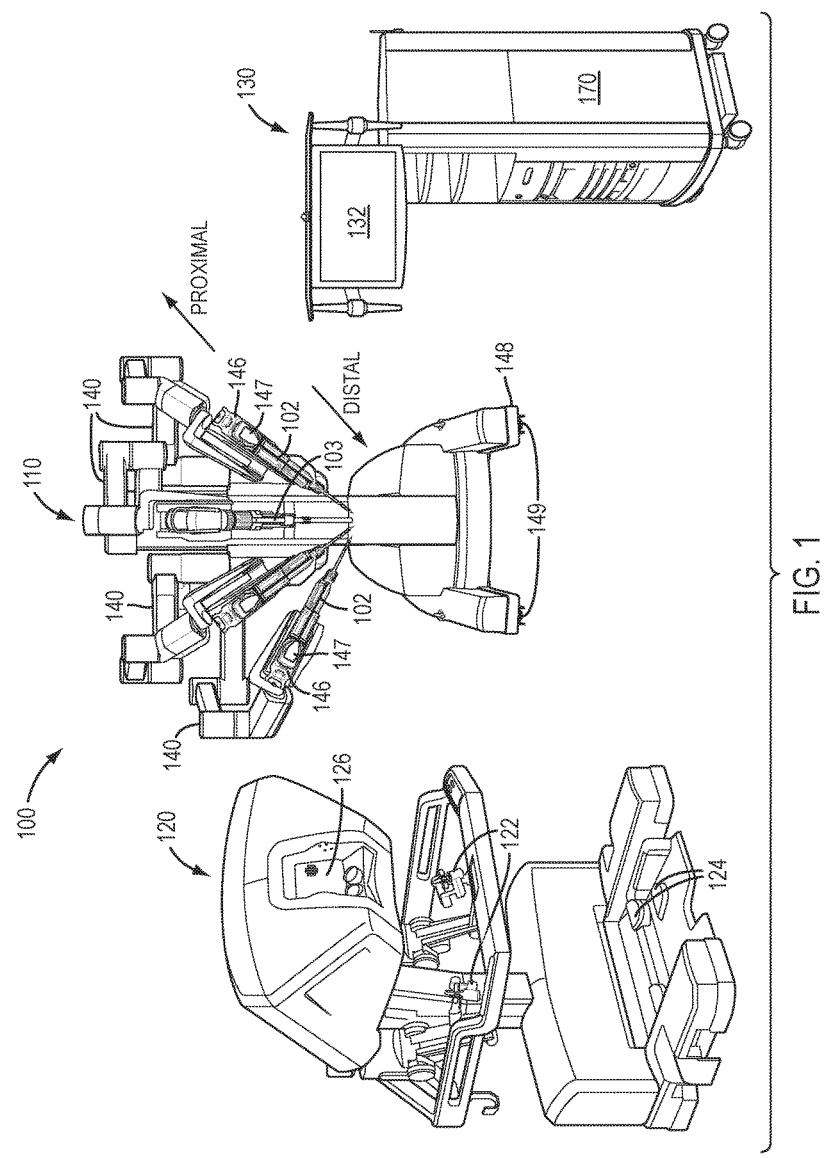
FIG. 1 is a diagrammatic view of an exemplary teleoperated surgical system in accordance with at least one exemplary embodiment.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Various exemplary embodiments contemplate a patient side cart of a teleoperated surgical system in which the patient side cart includes a steering interface for a user. The steering interface may permit a user to move the patient side cart in a relatively easy manner without the use of complex control devices. A steering interface in accordance with various exemplary embodiments may include "intelligence" in that they store various calibration data that can be provided to a control processor that uses drive control algorithms for motor-assisted driving of the cart. Such data may be used for various purposes, such as to calibrate devices of the steering interface which may vary to a degree from one to another. For instance, data could include calibration data for one or more sensors that are included in the steering interface. Calibration of a component of a steering interface, such as a force sensor, may include storing calibration data in a data storage device of the steering interface. The calibration may include, for instance, data that associates a force detected by a force sensor with a signal that a drive system of a cart may use to control movement of a cart. The calibration data may associate the detected force with a signal for a drive system through an algorithm, such as through one or more equations, look up tables, or other functions. The features of the exemplary embodiments described herein may be applied to other wheeled objects, such as, for example, imaging equipment, operating tables, and other wheeled devices which are intended to move through the application of a motive force (e.g., pushing and/or steering forces) by a user.

Further, the intelligence functions of the steering interface may be configured to function automatically, such as when a steering interface is initially mounted to a cart and connections are made between the cart and steering interface to permit transmittal of data to the cart. For instance, the calibration function of a steering interface may function automatically when the steering interface is mounted to a cart, causing stored data from a calibration device of the steering interface to calibrate signals transmitted from one or more force sensors to a drive system of the cart.

In various exemplary embodiments, the steering interface may be replaceable, e.g., in the field, such as when the steering interface or component thereof is damaged or otherwise non-functional. In addition, if one or more components of a steering interface is damaged or otherwise requires repair, the steering interface could be removed so the component may be repaired or replaced. Recalibration could also be conducted on components of a steering interface once the steering interface has been removed so that the steering interface is ready to function when the steering interface is attached to a cart. According to an exemplary embodiment, steering interfaces described herein may be used with various carts, including carts of different sizes and/or configurations. Further, various exemplary embodiments contemplate a steering interface for a patient side cart of a teleoperated surgical system.

Steering interfaces of the exemplary embodiments described herein may be provided in various forms. According to one exemplary embodiment, a steering interface for a patient side cart of a teleoperated surgical system may be provided in the form of a handlebar. However, the form or shape of the steering interface for a user of a patient side cart of a teleoperated surgical system is not limited to this exemplary embodiment. For example, a steering interface for a patient side cart may be in the form of a plurality of handlebars, one or more handles, a steering wheel, combinations of these interfaces, and other shapes and forms used for steering interfaces.

Teleoperated Surgical System

With reference now to FIG. 1, a teleoperated surgical system 100 is provided which, in an exemplary embodiment, performs minimally invasive surgical procedures by interfacing with and controlling a variety of remotely operated surgical instruments, such as one or more electrosurgical instruments 102, as those of ordinary skill in the art are generally familiar. The surgical instruments 102 may be selected from a variety of instruments that are configured to perform various surgical procedures, and in accordance with various exemplary embodiments can have a variety of configurations to implement surgical procedures of conventional surgical instruments. Non-limiting examples of the surgical instruments 102 include, are but not limited to, instruments configured for suturing, stapling, grasping, applying electrosurgical energy, and a variety of other instruments with which those having ordinary skill in the art are generally familiar.

As illustrated in the schematic view of FIG. 1, the teleoperated surgical system 100 includes a patient side cart 110, a surgeon console 120, and a control cart 130. In non-limiting exemplary embodiments of the teleoperated surgical system, the control cart 130 includes "core" processing equipment, such as core processor 170, and/or other auxiliary processing equipment, which may be incorporated into or physically supported at the control cart 130. The control cart 130 may also include other controls for operating the teleoperated surgical system. As will be discussed in more detail below, in an exemplary embodiment, signals transmitted from surgeon console 120 may be transmitted to one or more processors at control cart 130, which may interpret the signals and generate commands to be transmitted to the patient side cart 110 to cause manipulation of one or more of surgical instruments and/or patient side manipulators 140a-140d to which the surgical instruments 102 are coupled at the patient side cart 110. It is noted that the system components in FIG. 1 are not shown in any particular positioning and can be arranged as desired, with the patient side cart 110 being disposed relative to the patient so as to affect surgery on the patient. A non-limiting, exemplary embodiment of a teleoperated surgical system with which the principles of the present disclosure may be utilized is a da Vinci® Si (model no. IS3000) commercialized by Intuitive Surgical, Inc. of Sunnyvale, Calif.

In general, the surgeon console 120 receives inputs from a user, e.g., a surgeon, by various input devices, including but not limited to, gripping mechanisms 122 and foot pedals 124, and serves as a master controller by which instruments mounted at the patient side cart 110 act as slaves to implement the desired motions of the surgical instrument(s) 102, and accordingly perform the desired surgical procedure. For example, while not being limited thereto, the gripping mechanisms 122 may act as "master" devices that may control the surgical instruments 102, which may act as the corresponding "slave" devices at the manipulator arms 140, and in particular control an end effector and/or wrist of the instrument as those having ordinary skill in the art are familiar with. Further, while not being limited thereto, the foot pedals 124 may be depressed to provide, for example, monopolar or bipolar electrosurgical energy to the instrument 102.

In various exemplary embodiments, suitable output units may include, but are not limited to, a viewer or display 126 that allows the surgeon to view a three-dimensional image of the surgical site, for example, during the surgical procedure, e.g., via an optical endoscope 103 at the patient side cart 110. Other output units may include a speaker (or other component capable of transmitting sound), and/or a component with which a surgeon is in contact that can vibrate or the like to provide haptic feedback. In various exemplary embodiments, the one or more output units may be part of the surgeon console 120 and signals can be transmitted from the control cart 130 thereto. Although in various exemplary embodiments, one or more input mechanisms 122, 124 may be integrated into the surgeon console 120, various other input mechanisms may be added separately and provided so as to be accessible to the surgeon during use of the system, but not necessarily integrated into the surgeon console 120. In the context of the present disclosure, such additional input mechanisms are considered part of the surgeon console.

Thus, a "surgeon console" as used herein includes a console that comprises one or more input devices 122, 124 that a surgeon can manipulate to transmit signals, generally through a control cart such as 130 to actuate a remotely-controllable kinematic structure (e.g., surgical instruments 102 mounted at arms 140) at the patient side cart 110. The surgeon console 120 may also include one or more output devices that can provide feedback to the surgeon. As used herein, it should be understood, however, that a surgeon console can include a unit (e.g., substantially as shown by element 120 in FIG. 1) that integrates the various input and output devices, with, for example, a display, but also can include separate input and/or output devices that are in signal communication with the controllers, such as controllers provided at the control cart and accessible by a surgeon, although not necessarily integrated within a unit with various other input devices. As an example, input units may be provided directly at the control cart 130 and may provide input signals to a processor at the control cart. As such, a "surgeon console" does not necessarily require all of the input and output devices to be integrated into a single unit and can include one or more separate input and/or output devices.

The exemplary embodiment of FIG. 1 illustrates a patient side cart 110 with multiple, independently moveable manipulator arms 140 that each supports an actuation interface assembly (such as, e.g., 146 shown in FIG. 3) and are configured to hold and manipulate various tools, including, but not limited to, for example, a surgical instrument (e.g., electrosurgical instruments 102), and an endoscope 103. However, those having ordinary skill in the art will appreciate that other patient side cart configurations may be used.

Based on the commands input to input devices at, for example, the surgeon console 120, the patient side cart 110 can position and actuate the instrument(s) 102 to perform a desired medical procedure via the actuation interface assemblies 146 at the manipulator arms 140. The actuation interface assemblies 146 are configured to engage with transmission mechanisms 147 provided at a proximal end of the surgical instruments 102 (the general "proximal" and "distal" directions being shown in FIG. 1 relative to the surgical instrument). The surgical instrument 102 and the actuation interface assembly 146 may be mechanically and/or electrically connected to be able to operate the instrument 102. A patient side cart 110 may include a plurality of wheels 149 mounted or otherwise attached to the cart 110, such as to a base 148 of the cart 110.

The teleoperated surgical system 100 can include a control system that receives and transmits various control signals to and from the patient side cart 110 and the surgeon console 120. The control system can transmit light and process images (e.g., from an endoscope at the patient side cart 110) for display, such as, e.g., display 126 at the surgeon console 120 and/or on a display 132 associated with the control cart 130.

In exemplary embodiments, the control system may have all control functions integrated in one or more processors, such as a core processor 170 at the control cart 130, or additional controllers (not shown) may be provided as separate units and/or supported (e.g., in shelves) on the control cart 130 for convenience. The latter may be useful, for example, when retrofitting existing control carts to control surgical instruments requiring additional functionality, for example, by providing electrical energy for use in monopolar and bipolar applications.

One of ordinary skill in the art would recognize that the controllers, e.g., core processor 170, provided at control cart 130 may be implemented as part of a control system, which, as will be discussed in more detail below, controls various functions of the present disclosure. One of ordinary skill in the art would recognize that functions and features of the controllers, e.g., core processor 170, may be distributed over several devices or software components, including, but not limited to, processors at any of the surgeon console 120, patient side cart 110 and/or other devices incorporating processors therein. Functions and features of the control system, which may include core processor 170, may be distributed across several processing devices.

Patient Side Cart Steering Interface

A teleoperated surgical system, such as system 100, may be used in a particular location during its use, such as in an operating room. On the other hand, there may be a need to move the teleoperated surgical system or some of its components. For example, a patient side cart 110 may need to be moved to a desired position during use, such as to locate the patient side cart 110 so that its surgical instruments 102 are positioned to perform surgery on a patient when controlled by a surgeon at a surgeon console 120. It also is desirable to move a patient side cart 100 away from the patient. Such positioning of a patient side cart 110 may require moving the patient side cart 110 within a given room or moving the patient side cart 110 from one room to another.

An exemplary patient side cart may have a weight in the range of one thousand to two thousand pounds, for example. In another example, an exemplary patient side cart may have a weight in the range of, for example, about 1200 pounds to about 1850 pounds. Without assistance, such a heavy patient side cart might be difficult for a user to move and control during its movement. One way to provide assistance in moving a patient side cart is to include a powered drive system in the patient side cart that is controlled on the basis of input provided by the user. However, a drive system could require several discrete controls that separately control a component of the motion of a patient side cart. For instance, the controls for a drive system could include a throttle control, a brake control, and/or steering controls each of which a user may have to manipulate during movement of a patient side cart. Such an array of various controls could present a user with some difficulty when moving a patient side cart, particularly when a user is not familiar with the drive controls of a patient side cart. Therefore, it may be desirable to provide a drive control for a patient side cart that is easy to use and provides input from a user to the patient side cart.

Figure 2:
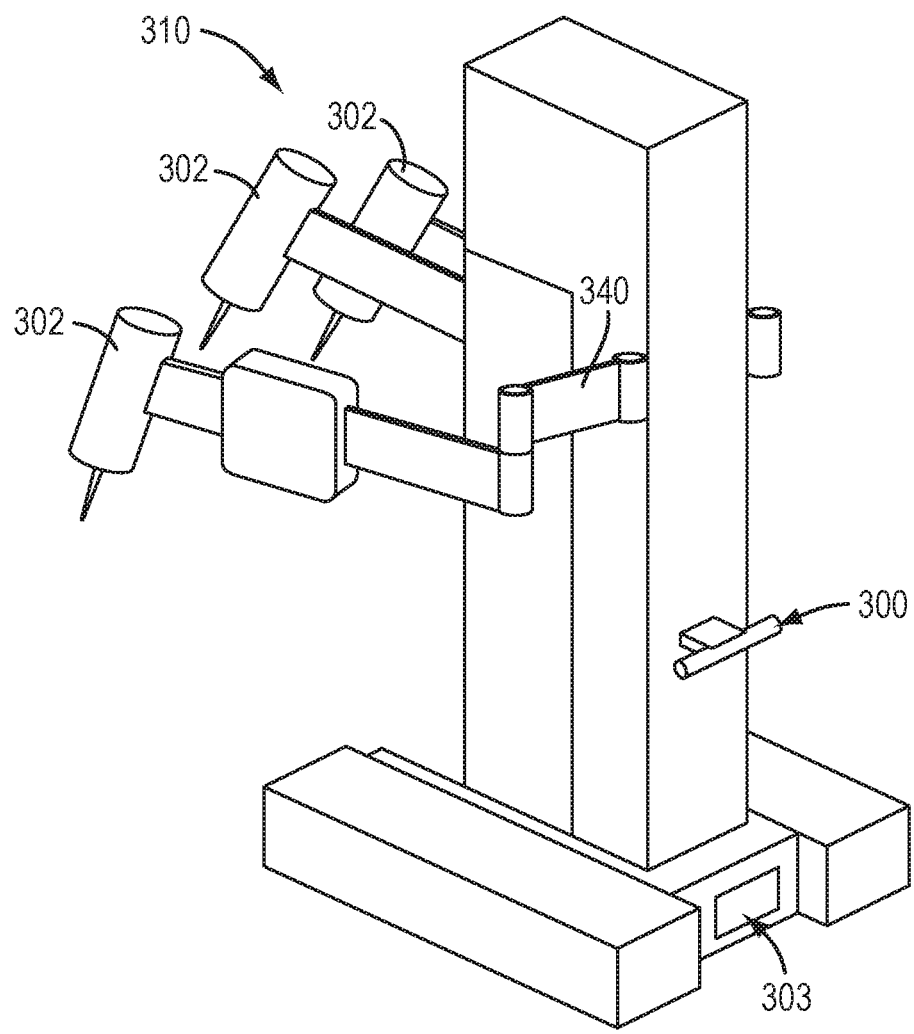
FIG. 2 is a schematic perspective view of an exemplary embodiment of a patient side cart that includes a steering interface.

Turning to FIG. 2, an exemplary embodiment of a patient side cart 310 is shown schematically. A patient side cart 310 may be arranged according to any of the exemplary embodiments described herein, such as with reference to FIG. 1 described above. For example, a patient side cart 310 may include one or more surgical instrument(s) 302 and one or more patient side manipulator(s) 340 to which the surgical instrument(s) 302 are coupled. A patient side cart 310 may include wheels (not shown) on its base to permit movement of the cart. For example, a patient side cart 310 may include three wheels or four wheels. One or more of the wheels may be driven by a drive system included in the patient side cart 310 that provides motive force to the driven wheel(s). For instance, in one exemplary embodiment, wheels in the front of a patient side cart may be driven while rear wheels are not, with the front of the cart being where the manipulator arms are positioned. In other examples, wheels in the rear of a patient side cart may be driven or all wheels of a patient side cart may be driven. Wheels that are not driven may be permitted to spin freely as the patient side cart is driven and the wheel contacts a ground surface. Wheels may also be turned by steering mechanisms according to steering input provided by a user. According to an exemplary embodiment, one or more wheels may have a configuration similar to a caster wheel and may be permitted to turn freely.

According to an exemplary embodiment, a patient side cart 310 of a teleoperated surgical system may include a steering interface 300, as shown in FIG. 2. A steering interface 300 may be used to detect forces applied by a user to the steering interface 300, which in turn may issue a signal to a controller of a drive system of a patient side cart 310, which causes the patient side cart 310 to be driven and steered in a desired manner. As shown in the example of FIG. 2, a steering interface 300 may be attached to a rear of a patient side cart 310, with one or more surgical instrument(s) 202 being located on a front end of the patient side cart 310. However, the exemplary embodiments described herein are not limited to a patient side cart 310 with a steering interface 300 attached to a rear, and the steering interface 300 may instead be mounted on other portions of a patient side cart 310, such as a front or side of the patient side cart 310.

Figure 3:
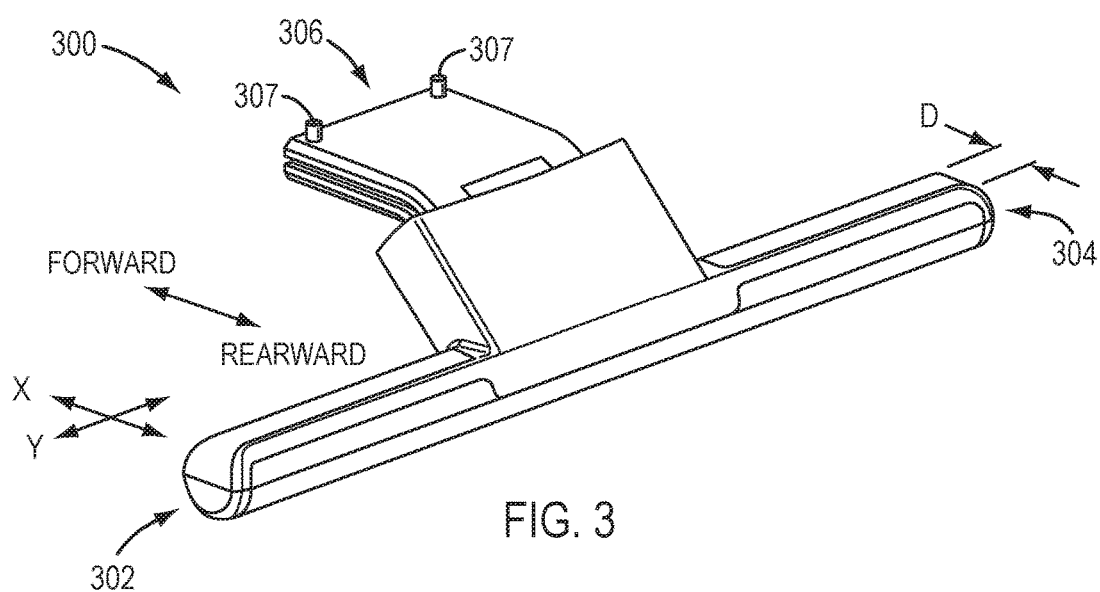
FIG. 3 is a front perspective view of an exemplary embodiment of a steering interface for a patient side cart.
Figure 4:
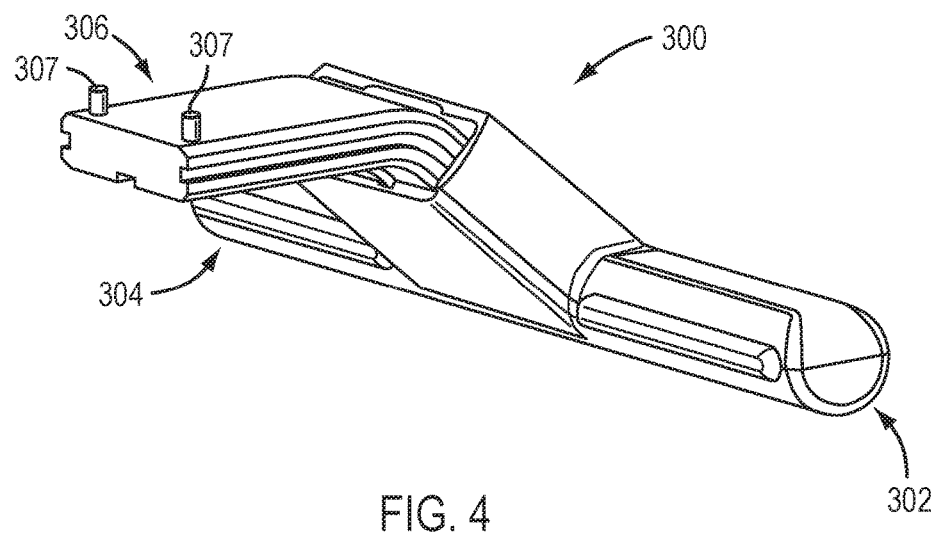
FIG. 4 is a rear perspective view of the steering interface of FIG. 3.

Turning to FIGS. 3 and 4, an exemplary embodiment of a steering interface 300 for a patient side cart of a teleoperated surgery system is shown. According to the exemplary embodiment shown in FIGS. 3 and 4, a steering interface 300 for a patient side cart of a teleoperated surgical system may be provided in the form of a handlebar. Such a handlebar may have a rounded transverse cross-section and be sized so as to provide a comfortable, yet firm, grip for a user steering the cart. In an exemplary embodiment, the handle 300 may have a maximum lateral dimension (e.g., diameter) D ranging from, for example, about 1 inch to about 2 inches. In another exemplary embodiment, the handle 300 may have a maximum lateral dimension (e.g., diameter) D of, for example, approximately 1.5 inches.

However, steering interfaces of the exemplary embodiments described herein may be provided in various forms and the form or shape of a steering interface for a user of a patient side cart of a teleoperated surgical system is not limited to this exemplary embodiment. For example, a steering interface for a patient side cart may be in the form of a plurality of handlebars, one or more handles, a steering wheel, combinations of these forms, and other shapes and forms used for steering interfaces.

According to an exemplary embodiment, a steering interface 300 may be detachable from a patient side cart. Configuring a steering interface 300 to be detachable permits a user to remove a damaged or otherwise non-functional steering interface 300 with another steering interface 300. For example, as shown in FIGS. 3 and 4, the steering interface 300 may include a mounting portion 306 that contacts a patient side cart and attaches the steering interface 300 to the patient side cart. To permit a user to replace a steering interface with relative ease, a steering interface 300 may include one or more devices to attach the steering interface 300 to a patient side cart. As shown in the exemplary embodiment of FIGS. 3 and 4, the mounting portion 306 of a steering interface 300 may include one or more fasteners 307 to attach the steering interface 300 to a patient side cart. Fasteners 307 may be, for example, threaded fasteners, such as bolts, or other types of fasteners that permit a user to detach the mounting portion 306 of a steering interface 300 from a patient side cart with relative ease. Therefore, when a user desires to replace a steering interface 300, the user may unfasten the mounting portion 306 of the steering interface 300 from a patient side cart, such as via the one or more fasteners 307, and attach a second steering interface (not shown) to the patient side cart via the mounting portion and fastener(s) of the second steering interface.

As will be described in further detail below, the steering interface 300 may have a core/shell configuration, with at least a portion of the core being located at in a region of the mounting portion 306 and the outer shell being located at least in a region of a left portion 302 of the steering interface and a right portion 304 of the steering interface.

To use a steering interface 300 of a patient side cart, a user may push the steering interface 300 in a direction that the user desires the patient side cart to move. Such a force may be applied to the steering interface 300 while grasping the steering interface 300. For example, when a steering interface 300 is provided in the form of a handlebar, as shown in the exemplary embodiment of FIGS. 3 and 4, a user may grasp a left portion 302 of the steering interface 300 and a right portion 304 of the steering interface 300. When the steering interface 300 is connected at a rear of a patient side cart 310, as shown in the example of FIG. 2, a user may push the steering interface 300 substantially in the forward direction shown in FIG. 3. The steering interface 300, as described in more detail below, may be configured to detect the force applied by the user in the forward direction and provide a signal to a control system of a drive system of the patient side cart 310 to move the patient side cart 310 in the forward direction.

Similarly, when a user wishes to move the patient side cart 310 in a rearward direction, the user may pull on the steering interface 300 substantially in the rearward direction shown in FIG. 3 so that the steering interface 300 may detect the force and provide a signal to the control system of the drive system so that the patient side cart 310 is moved in the rearward direction.

According to an exemplary embodiment, a user may indicate a desire to turn a patient side in a given direction by applying a force to a steering interface of the cart. For instance, a user may apply a lateral force to a steering interface 300 along directions substantially perpendicular to the forward and rearward directions of FIG. 3, which may substantially correspond to a direction along a Y direction or axis.

The sensor configuration discussed above for detection of a force applied by a user to indicate a desired movement for a patient side cart is one exemplary way of sensing turning and fore/aft steering control, but other techniques also could be employed and sensor configurations modified accordingly. For instance, according to another exemplary embodiment, a user may indicate that the patient side cart should turn by applying more force to one of the left portion 302 and right portion 304 of the steering interface 300 than the other of the left portion 302 and right portion 304. The steering interface 300 can detect the applied forces and issue a signal to the control system of the drive system, which commands the drive system to turn in the direction desired by the user.

As noted above, the steering interface 300 may include one or more sensors configured to detect forces applied to the steering interface 300 by a user. Turning to the exemplary embodiment of FIG. 5, the steering interface 300 is depicted with its outer shell removed to show internal components of the steering interface 300, including a core portion 310. The core portion 310 may be constructed from a material capable of withstanding relatively high stress. For example, the core portion 310 may be manufactured from a high strength steel, but other high strength materials also may be used without departing from the scope of the present disclosure. In an exemplary embodiment, the outer shell may be manufactured from, for example, a metal or metal alloy, such as aluminum. According to an exemplary embodiment, an outer shell may include materials at locations corresponding to where a user may touch or grasp the handle to provide a desirable tactile feel for a user. For instance, an outer shell may include rubber, plastic, or other materials at such locations.

Figure 5:
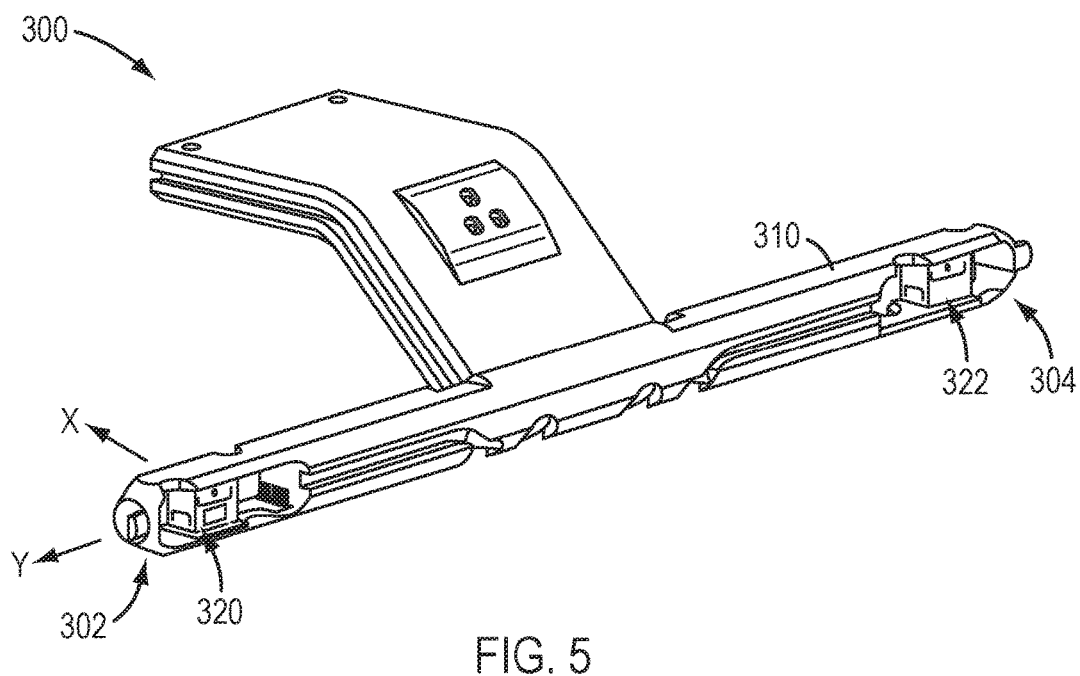
FIG. 5 is an interior perspective view of an exemplary embodiment of a steering interface.

The core portion 310 of the steering interface 300 may include one or more sensors configured to transmit signals to a drive system (not shown) of the cart to move the cart upon input by a user at the steering interface 300. For example, as shown in FIG. 5, a steering interface 300 may include a first sensor 320 mounted in a left portion 302 of the steering interface 300 and a second sensor 322 mounted in a right portion 304 of the steering interface 300. In other words, sensors 320, 322 may be provided in substantially opposite portions of a steering interface 300. By providing a steering interface 300 with sensors 320, 322 in different portions of the interface 300, a user may advantageously position themselves at differing positions relative to the steering interface 300 and apply a force with one or both hands and thus apply a force to one or both of sensors 320, 322 to achieve the same result with respect to the steering and movement of the cart. Such a configuration can be helpful, for instance, to facilitate the ability of a user to observe the environment in front of the cart when a user is positioned at the rear of the cart. If the user were required to be positioned directly behind the cart to operate the steering interface 300, the user's view may be blocked by the cart, such as by the manipulator arm portion of the cart. By permitting a user to be positioned relatively to one side of the steering interface 300, the user may stand to one side of the cart, use one hand on the steering interface 300, and have an improved view of the environment in front of the cart.

Sensors 320, 322 may be configured to detect forces applied to the steering interface 300 by a user in the forward and rearward directions of FIG. 3 and may be configured to detect forces applied by a user to the steering interface 300 to turn a patient side cart 310. The forward and rearward directions of FIG. 3 may substantially correspond to directions along an X direction or axis and directions substantially perpendicular to the forward and rearward directions of FIG. 3 may substantially correspond to directions along a Y direction or axis.

Figure 6:
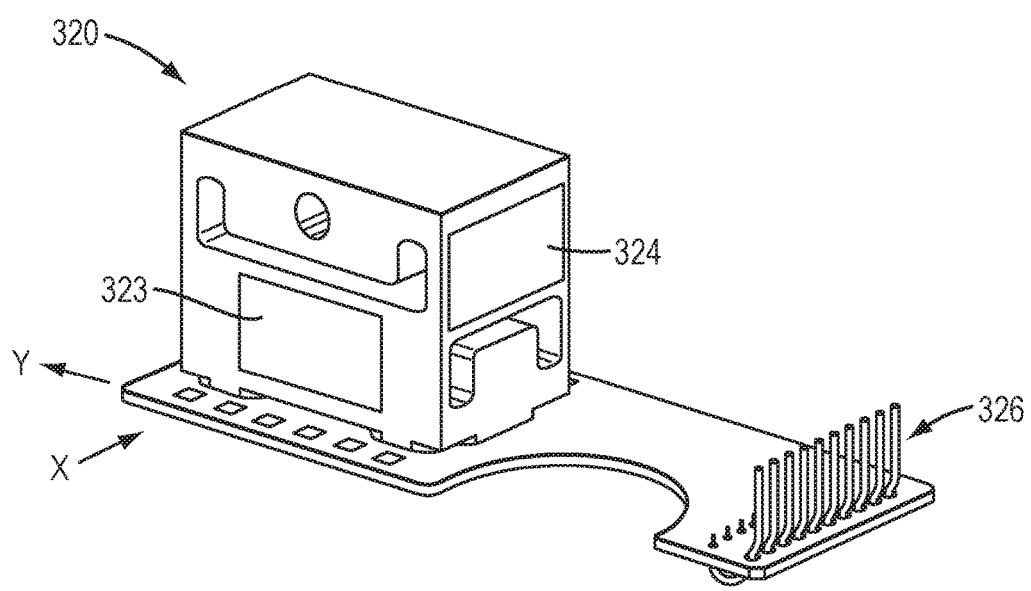
FIG. 6 is a perspective view of an exemplary embodiment of a sensor for a steering interface.

Turning to FIG. 6, an exemplary embodiment of a first sensor 320 is shown. Although the following discussion concerns the structures and features of first sensor 320, which may be mounted at the left portion 302 of a steering interface 300, second sensor 322, which may be mounted at the right portion 304 of the steering interface 300, may have the same features and structures as first sensor 320.

Because forces applied by a user may include components in the X and/or Y direction indicated in FIG. 5, sensor 320 may include features to detect forces in one or more directions. According to an exemplary embodiment, sensor 320 may include features to detect forces in the X and Y directions indicated in FIGS. 5 and 6. For example, sensor 320 may include a first detection device 323 to measure forces applied by a user along the X direction of FIGS. 5 and 6 and a second detection device 324 to measure forces applied by a user along the Y direction of FIGS. 5 and 6. As indicated in FIGS. 5 and 6, the X direction and Y direction may be orthogonal to one another. Therefore, even if a force applied by a user to a steering interface 300 is not perfectly aligned with either of the X and Y directions, the components of the applied force may be measured in the X and Y directions.

In various exemplary embodiments, sensors used in a steering interface also may be capable of detecting forces in a vertical Z direction (not shown in the embodiments of FIGS. 5 and 6), which is orthogonal to the X and Y directions. However, sensors capable of detecting forces in a vertical Z direction are optional and a steering interface may include only sensors that detect forces in the X and Y directions.

Detection devices 323, 324 may be configured to detect relatively small forces applied by a user to a steering interface 300, such as when a user pushes, pulls, or moves sideways the steering interface 300 to indicate a desire to move a patient side cart. For example, detection devices 323, 324 may be sufficiently sensitive to detect a force applied by a person to a steering interface 300. For example, detection devices 323, 324 may be sensitive enough to detect a force applied by a person having the weight and size of an average adult. According to an exemplary embodiment, detection devices 323, 324 may detect forces ranging from, for example, from approximately 0.1 lbs. to approximately 100 lbs. According to another exemplary embodiment, detection devices 323, 324 may detect forces ranging from, for example, from approximately 0.4 lbs. to approximately 25 lbs. According to exemplary embodiments, the range of force sensitivity of the sensors may be selected based on factors such as, for example, the size and/or weight of the cart and/or the exertion desired to be required by a user during movement of the cart.

Detection devices 323, 324 of sensor 320 may be components configured to detect a force applied to sensor 320 and provide an electrical signal corresponding to the applied force. For instance, detection devices 323, 324 may be strain gauges. Each detection device 323, 324 may be a single device to measure an applied force or may include a plurality of devices to detect an applied force.

According to an exemplary embodiment, detection devices 323, 324 may each include a plurality of devices to detect applied forces in the X and Y directions so that sensors 320, 322 have redundant detection devices in case one of the detection devices of a sensor fails. For example, detection device 323 and/or detection device 324 may include primary and secondary detection components (not shown) in each of the X and Y directions to advantageously provide redundant detection devices.

Thus, if one of the primary or secondary detection components of a detection device 323, 324 should fail (including the connections or control electronics for one of the primary or secondary detection components), the detection component 323, 324 will have the other of the primary and secondary detection component functioning and will still be able to perform its function of detecting forces applied to a steering interface 300. In other words, the redundant primary or secondary detection components of a detection device 323, 324 may serve as a safety precaution that may prevent or minimize unanticipated cart movement, for example, by restricting cart movement if primary and secondary detection components are not in agreement. According to another exemplary embodiment, a secondary detection component may be provided as a redundant backup to the primary detection component, or vice versa. In this case, if one of the primary or secondary detection components of a detection device 323, 324 should fail, an entire sensor 320, 322 or steering interface 300 need not be replaced. In a further example, detection device 223 may include a primary strain gauge and a secondary strain gauge to detect forces in the X direction and detection device 224 may include a primary strain gauge and a secondary strain gauge to detect forces in the Y direction.

Figure 7:
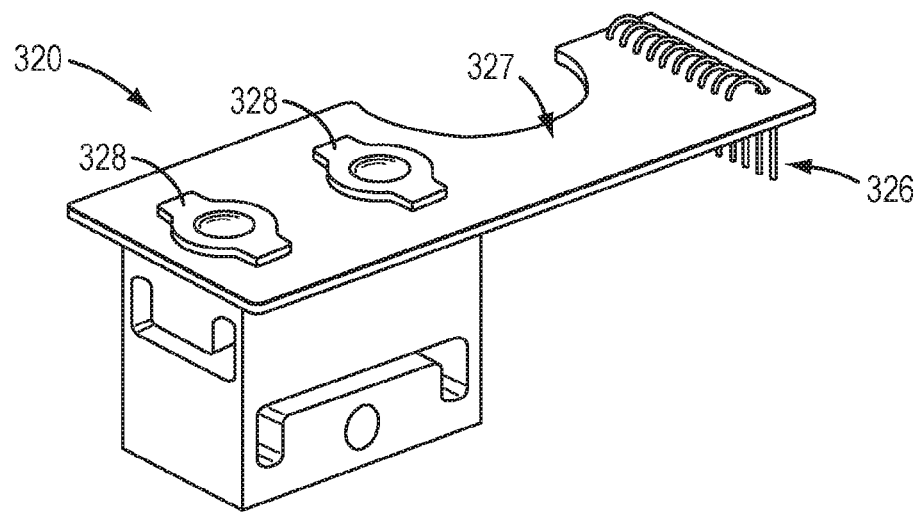
FIG. 7 is a bottom perspective view of the sensor of FIG. 6.

According to an exemplary embodiment, sensor 320 may further include one or more electrical terminals 326 that may be used to transmit electrical signals to and from the sensor 320. As shown in the example of FIG. 7, a bottom surface 327 of sensor 320 may include one or more mounts 328 to attach sensor 320 to a steering interface 300, such as a core portion 310 of a steering interface 300.

Because sensors 320, 322 are subjected to forces and strain when a user applies forces to a steering interface 300, it is possible that the sensors 320, 322 may become damaged, in particular because some strain gauge sensors are designed to detect relatively small displacements (e.g., forces) and the forces applied to the steering interface may be relatively large. To address this issue, sensors 320, 322 may be mounted in a steering interface 300 with one or more devices to provide a degree of protection to sensors 320, 322 by limiting excess forces on the sensors that could potentially damage the sensors 320, 322. Such protective devices can be any of a variety of devices that are compliant and bend. In addition, protective devices may limit the amount of movement that a sensor is permitted. In other words, one or more protective devices can be used to translate a relatively large displacement applied to a steering interface into a relatively small displacement of a sensor 320, 322. Such devices may include, for example, springs, bars or rods configured to deflect (e.g., through bending and/or torsion), elastomer material, and other types of devices configured to provide additional compliance around the sensors 320, 322 when the shell portion 312 moves relative to the core portion 310.

Figure 8:
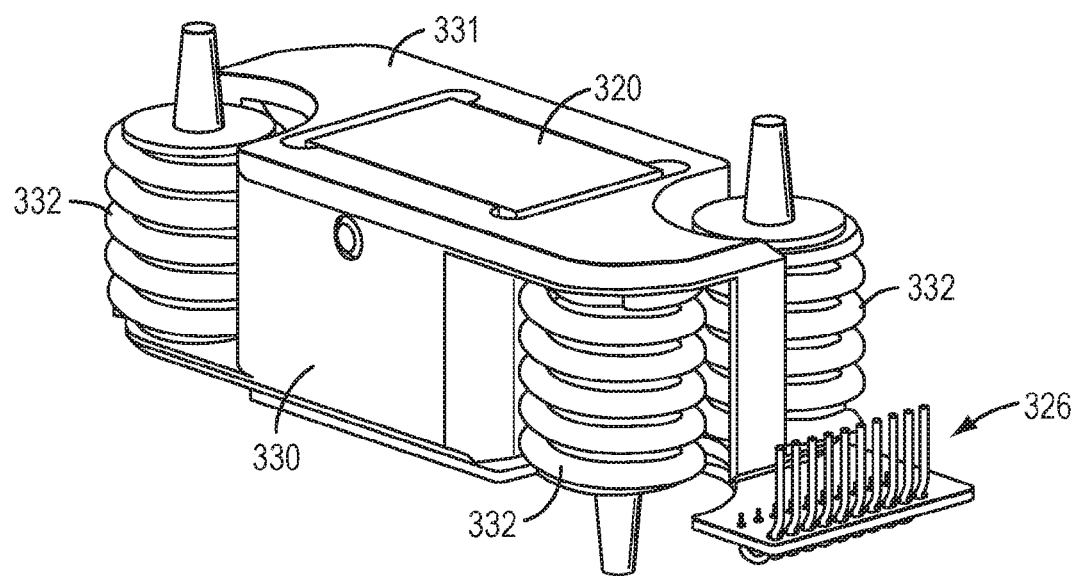
FIG. 8 is a perspective view of an exemplary embodiment of a sensor block for a steering interface.

For example, as shown in the exemplary embodiment of FIG. 8, sensor 320 may be mounted with one or more springs 332 configured and arranged relative to the sensor 320 to provide a degree of protection to sensor 320. Sensor 320, a sensor housing 331, and springs 332 together may form a sensor block 330, which may be mounted within a steering interface 300 via the spring(s) 332 so that the spring(s) provide additional compliance between the sensor 320 and the remainder of the steering interface 300.

Figure 9:
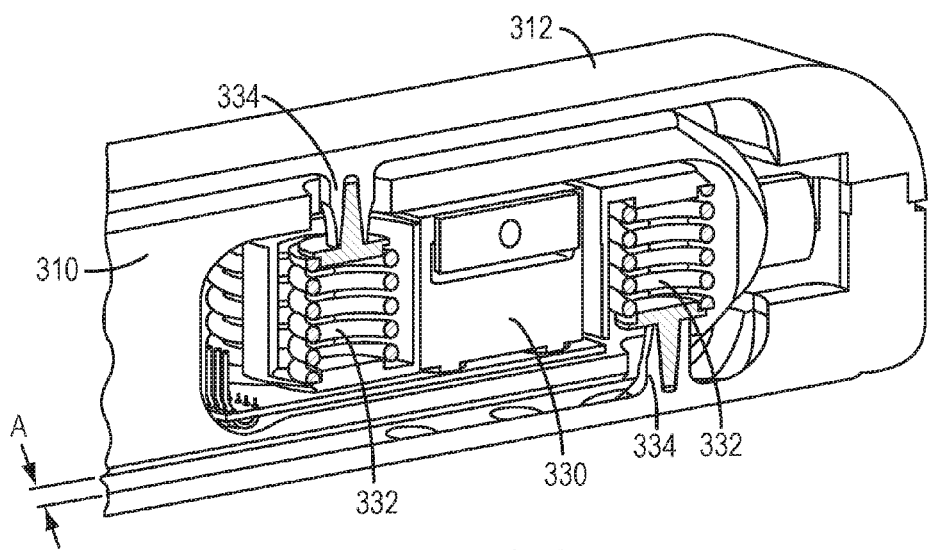
FIG. 9 is a cross-sectional perspective view of an exemplary embodiment of a steering interface and a sensor block mounted within the steering interface.

For instance, as shown in the exemplary embodiment of FIG. 9, sensor block 330 (shown in section in FIG. 9) may be included in a steering interface 300 by mounting sensor 320 to a core portion 310 of the steering interface 300 and by attaching one or more springs 332 to a cover portion 312 of the steering interface 300 via one or more spring mounts 334. In other words, spring(s) 332 may connect sensor 320 to the cover portion 312. A cover portion 312 may be, for example, in the form of a shell around the core portion 310 (as shown in the example of FIG. 9), in the form of one more flat or curved surfaces, or other forms of a cover.

According to an exemplary embodiment, the core portion 310 and the cover portion 312 of the steering interface 200 may lack structural connections aside from those provided by the sensor blocks 330 of sensors 320, 322. In such an embodiment, therefore, the structural connections provided by the sensor blocks 330 of the one or more sensors of a steering interface 300 may provide the only connections between the core portion 310 and the cover portion 312 of a steering interface 300. In other words, if a steering interface 300 includes a single sensor block 330, the sensor block 330 may provide the sole connection between the core portion 310 and the cover portion 12. If a steering interface 300 includes a plurality of sensor blocks 330, the sensor blocks 330 may collectively provide the sole connection between the core portion 310 and the cover portion 312. For instance, connection provided by spring(s) 332, housing 331, and spring mount(s) 334 of a sensor block 330 may provide the sole connection between a core portion 310 and a cover portion 312. In this manner, the cover portion 312 and the core portion 310 may be considered to be "floating" relative to one another. According to an exemplary embodiment, the cover portion 312 may be considered to be "floating" relative to the core portion 310 due to the suspension of the cover portion 312 from the core portion 310 by the sensor block(s) 330. For instance, if the core portion 310 is connected to a patient side cart, the cover portion 312 may seem to move relative to the core portion 310. According to another exemplary embodiment, the core portion 310 may be considered to be floating relative to the cover portion 312, such as when the cover portion 312 is connected to a patient side cart instead of the core portion 310.

When a force is applied to a steering interface, for example to indicate a user's desired direction of movement of the cart, the force may be applied to the cover portion 312 and transmitted to the sensor 320 via spring(s) 332 due to the suspension structure provided by the sensor block(s) 330 arranged between the core portion 310 and the cover portion 312. Because spring(s) 332 are relatively flexible elements, spring(s) 332 may advantageously allow additional motion of the cover portion 312 relative to the core portion 310 for a same user-applied force. As a result, the sensor block 330 may be mounted between the core portion 310 and the cover portion 312 of the steering interface 300, with the spring(s) 332 serving to provide additional compliance to the steering interface 300.

As shown in FIG. 9, in various exemplary embodiments, a gap having a distance A may be provided between the core portion 310 and the cover portion 312. The gap may be provided between the core portion 310 and the cover portion 312 in all directions. The gap may have a distance A, for example, ranging from about 0.04 in. to about 0.07 in. In another example, the gap may have a distance A ranging from about 0.045 in. to about 0.065 in. A relatively small gap between the core portion 310 and the cover portion 312 may permit the cover portion 312 and the core portion 310 to move relative to one another. Such relative movement may enable forces applied by a user to be relatively easily transmitted to the sensors 320, 322. Providing a steering interface 300 with such construction may advantageously avoid a steering interface that is relatively "soft" (e.g., permits a higher degree of relatively movement between the core portion 310 and the cover portion 312), which could result in an undesirable feedback loop that may cause a significant change in an applied force to a sensor and result in the motion of a patient side cart to unintentionally oscillate. Further, according to an exemplary embodiment, the gap is sufficiently small so that movement between the core portion 310 and the cover portion 312 is imperceptible or negligible to human senses. Thus, a user might not notice movement of the cover portion 312 relative to the core portion 310, which in turn may impart a sturdy, high quality feel to the user during application of forces to the steering interface while driving the cart. Thus, the steering interface 300 may be able to provide its function of detecting forces applied by a user while also presenting an appearance of solid construction and craftsmanship.

Figure 10:
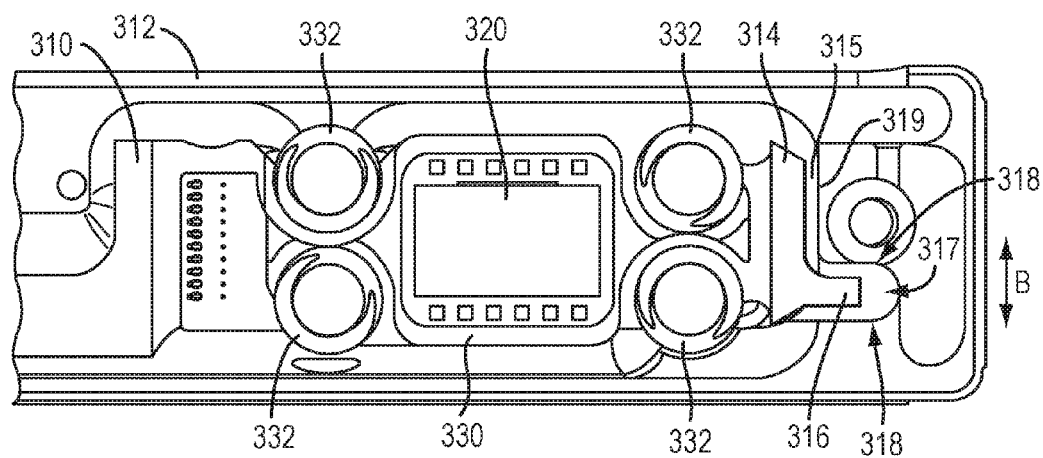
FIG. 10 is a cross-sectional view of an exemplary embodiment of a steering interface and sensor block mounted within the steering interface.

According to an exemplary embodiment, a steering interface 300 may include mechanical stops to limit the amount of relative movement between the core portion 310 and the cover portion 312 due to a force applied by a user to the steering interface 300. Thus, the mechanical stops may limit the amount of force and strain applied to sensors. Turning to the partial, internal plan view of FIG. 10, which shows the cover portion 312 of the steering interface 300 is suspended from a core portion 310 by a sensor block 330 and its spring(s) 332, as described above, end portion 314 of the core portion 310 may include a projection 316 that extends into a recess 317 formed within the cover portion 312 so that a gap 318 is provided between the projection 316 and an inner surface portion of the cover portion 312 surrounding the recess 317. In addition, a gap 315 may be provided between the end portion 314 of the core portion 310 and an inner wall 319 of the cover portion 312.

When a relatively large force is applied to a steering interface 300, the applied force may be applied to the sensor 320 of the sensor block 330. This may result in a large strain being applied to the sensor 320, which could cause damage to the sensor 320 if the strain is excessive. The relatively large force and strain may also move the core portion 310 and the cover portion 312 relative to one another, potentially causing the projection 316 to contact the wall of the cover portion 312 forming the recess 317. Alternatively, or in addition to this movement, the end portion 314 may come into contact with the inner surface portion 319. When the projection 316 contacts the inner surface portion of the cover portion 312 forming the recess 317 and/or the end portion 314 contacts the inner wall 319, further movement between the core portion 310 and the cover portion 312 is ceased so that the amount of strain applied to sensor 320 is limited. As a result, overloading and damage caused to the sensor 320 by large forces and strains may be minimized or prevented. In addition, springs 332 provide enhanced compliance for a sensor block 330. Thus, a sensor block 330 may have a cost effective design that permits reasonable manufacturing tolerances in gaps between core portion 310 and cover portion 312, while limiting displacement of a sensor 320 to a relatively small amount. For example, in an exemplary embodiment, a movement of about 0.065 inches between core portion 310 and cover portion 312 may result in a displacement of sensor 320 of about 0.010 inches.

According to an exemplary embodiment, sensors 320, 322 and their respective sensor blocks 330 may be contained within a steering interface 300 so that the sensors 320, 322 and sensor blocks 330 are completely surrounded. As a result, the sensors 320, 322 and sensor blocks may be covered and not exposed on an exterior surface of the steering interface 300. For instance, cover portion 312 of a steering interface 300 may completely surround sensors 320, 322 so that the sensors are not exposed, for example to the external environment. In another example, a portion of sensors 320, 322 may be exposed on an exterior surface of a steering interface 300 so that at least a portion of the sensors 320, 322 are able to be viewed by a user.

According to an exemplary embodiment, a steering interface 300 may include one or more devices to control the flexibility and movement of the steering interface 300 when a user applies a force to the steering interface 300. Such devices may be used, for example, to affect how the steering interface 300 moves relative to a patient side cart that the steering interface 300 is attached to when a user applies a force to the steering interface 300. Such devices may be provided in addition to the sensor blocks 330 described above, including the spring(s) 332 of a sensor block 330.

Figure 11:
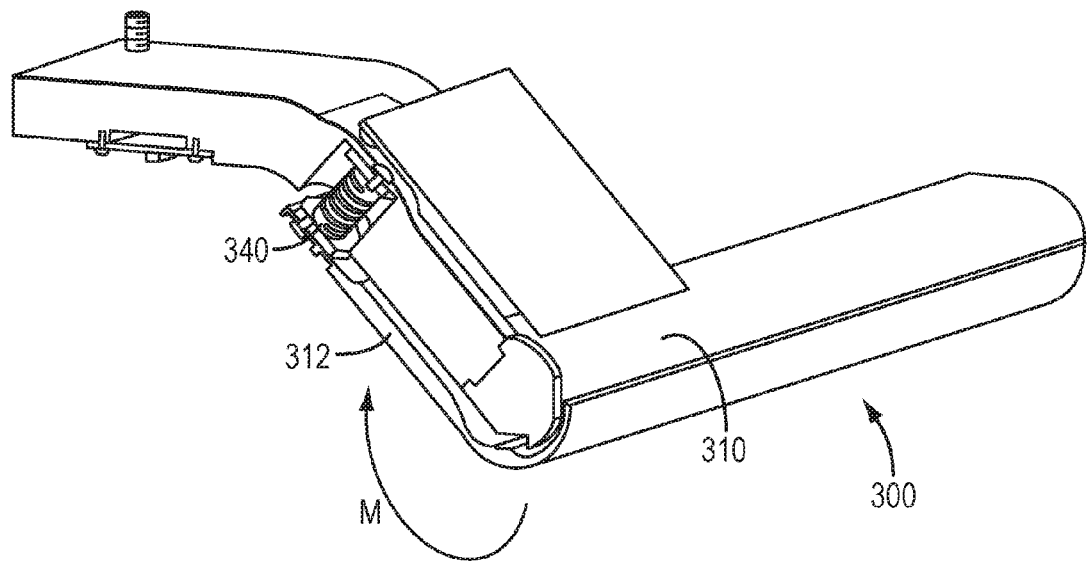
FIG. 11 is a cross-sectional perspective view of an exemplary embodiment of a steering interface.

Turning to FIG. 11, an exemplary embodiment of a steering interface 300 is shown in which a stabilizing device 340 is located between a core portion 310 and a cover portion 312 of the steering interface 300. According to an exemplary embodiment, a stabilizing device 340 may prevent motion of a steering interface in a direction other than an X or Y direction. Further, the stabilizing device 340 may be provided to control the amount of movement of cover portion 312 relative to core portion 310. For instance, a user may apply a rotational moment M to steering interface 300, as shown in the exemplary embodiment of FIG. 11. If a steering interface 300 moves in the direction indicated by moment M relative to a patient side cart, a user may have an impression that a patient side cart should respond in some manner as a result of the movement of the steering interface 300. Accordingly, using a stabilizing device to minimize or prevent such movement can avoid a user mistakenly believing that the cart will respond to such input at the steering interface 300. In addition, if the steering interface 300 moves in the direction indicated by moment M relative to a patient side cart that the steering interface 300 is mounted to, the user may have the sensation that the steering interface 300 is loose or not well made, particularly if the motion is abrupt and not smooth.

The stabilizing device 340 may act to resist motions that result when a user applies a force to a steering interface 300, which may cause the steering interface 300 to move in a direction away from its initial position (e.g., in the direction caused by moment M in FIG. 11), and a motion that results when the user releases the applied force, which may cause the steering interface 300 to move in a direction toward its initial position. For example, a stabilizing device 340 may resist motion by shunting an amount force ranging from, for example, about 10% to about 15% of the applied force to the core portion 310. Further, this shunting function of a stabilizing device 340 may act to permit motions of a steering interface substantially in linear directions along the X, Y, and Z directions. By acting in a manner that resists these motions, a stabilizing device 340 may permit the motions to occur but in a manner that results in smooth motions that are ergonomically desirable to a user, rather than abrupt, jerky motions. As shown in the exemplary embodiment of FIG. 11, an attenuating device 340 may be, for example, a coil spring mounted between the core portion 310 and the cover portion 312 of a steering interface 200. In a further example, a spring may be a machined spring or any of a variety of shock absorption mechanisms with which those having skill in the art have familiarity. Other mechanisms may be used as a stabilizing device other than springs. In an exemplary embodiment, a stabilizing device 340 may be provided by using a pair of permanent magnets.

According to an exemplary embodiment, a steering interface 300 may include a device to send a signal to a drive control system of a patient side cart to activate motion for the cart. For instance, although sensor(s) of a steering interface may always send signals regarding forces applied to the steering interface, it may be desirable to provide a device that provides a signal to indicate that motion of a patient side cart should not occur to prevent inadvertent motion of a cart, even if sensor(s) are indicating that a force is being applied to the steering interface. In other words, a steering interface may include a second device that issues a second signal that is independent to a first signal issued by sensor(s) of the steering interface. If a force applied to a second device of a steering interface has a sufficient magnitude, the second device may issue a signal indicating that the applied force represents a desired movement. Otherwise, if the force applied to the second device is not sufficient, the second device will not issue a signal to indicate that the cart should move. Such a device may provide a degree of safety by preventing inadvertent motion of a cart when signals are being issued from sensor(s) of the steering interface 300 to the controller for the drive system of a cart and a user is not applying a force to the steering interface 300 or a force applied to the steering interface 300 does not represent a desired motion for the cart.

Figure 12:
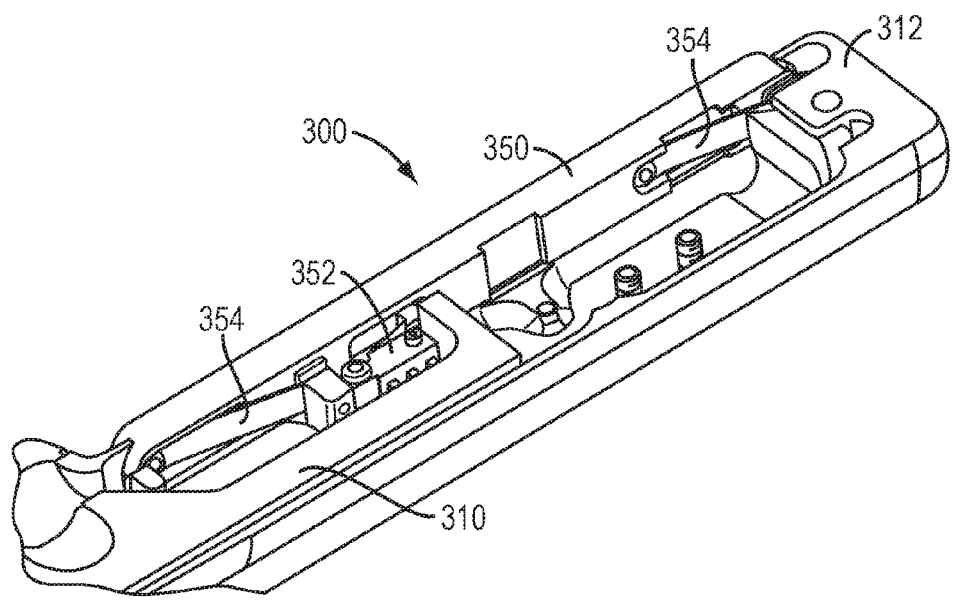
FIG. 12 is a cross-sectional perspective view of an exemplary embodiment of a steering interface including a contact switch.

Turning to FIG. 12, an example of a steering interface 300 is shown that includes a contact switch 352 and a contact trigger 350. The contact switch 352 and contact trigger 350 may be mounted within the steering interface 300 to permit relative movement between the contact switch 352 and the contact trigger 350. In particular, a contact trigger 350 and a contact switch 352 may both be mounted in a cover portion 312, with at least a portion of the contact trigger 350 exposed on an outer surface of the cover portion 312 so that a user may press the exposed portion of the contact trigger 350 to cause the contact trigger 350 to move relative to the contact switch 352 and cause engagement between the trigger 350 and switch 352.

When a user applies a force to a steering interface 300, relative motion may occur between a core portion 310 and a cover portion 312 of the steering interface 300 and sensor(s) 320 of the steering interface 300 may issue a signal indicating the applied force. However, such an applied force may not result in movement of the cart if trigger 350 is not properly engaged. To indicate a desired movement for a patient side cart, a contact trigger 350 may be pressed to cause engagement between the contact trigger 350 and the contact switch 352. When a sufficient force is applied to the contact trigger 350 to cause engagement between the trigger 350 and the switch 352, the contact switch 352 may issue a signal to a controller or drive system of a patient side cart to indicate that the patient side cart should move according to a signal issued from sensor(s) of the steering interface. Thus, the contact switch 352 and the contact trigger 350 may serve as a "dead man's" switch so that motion of a patient side cart is permitted when a user applies a force to a steering interface 300 and presses the trigger 350, but motion is not permitted when the user releases the trigger 350 or otherwise does not apply a force to the trigger 350.

When the contact switch 352 and the contact trigger 350 are not engaged, the steering interface 300, such as the contact switch 352, may issue a signal indicating that a patient side cart should not move according to a signal issued by sensor(s) of the steering interface 300 so that inadvertent motion of the cart is avoided. Alternatively, when contact switch 352 and contact trigger 350 are not engaged, no signal may be issued from the steering interface 300, such as from the contact switch 352, to indicate that a patient side cart should move, and the absence of such a signal may be interpreted by a controller or drive system of a cart that motion should not occur.

In a further example, at least one of the contact switch 352 and the contact trigger 350 may be mounted such that the contact trigger 350 is biased to an "off" position when a user does not apply a force to the contract trigger 350. In an exemplary embodiment, the contact trigger 350 may be mounted using one or more leaf springs 354, although such biasing devices are exemplary and non-limiting only. In another exemplary embodiment, the contact trigger 350 may be mounted using a pivoting lever with a return spring (not shown), such as a coil spring, a spring loaded pushbutton, or other structure including an elastically deformable structure.

A steering interface 300 may include a plurality of contact switches 352 and contact triggers 350. For example, each of the left portion 302 and the right portion 304 of a steering interface 300 may include a contact switch 352 and a contact trigger 350 so that a user may press either a trigger of the left portion 302 or a trigger of the right portion 304 of the steering interface 300 to activate motion of a patient side cart that the steering interface 300 is mounted to. In an alternative exemplary embodiment, the steering interface 300 may be configured to require more than one of the contact triggers to be actuated to activate motion of the cart. Further, trigger 350 need not be in the form of a mechanical contact but may take the form of other switch devices used in the art.

Figure 13:
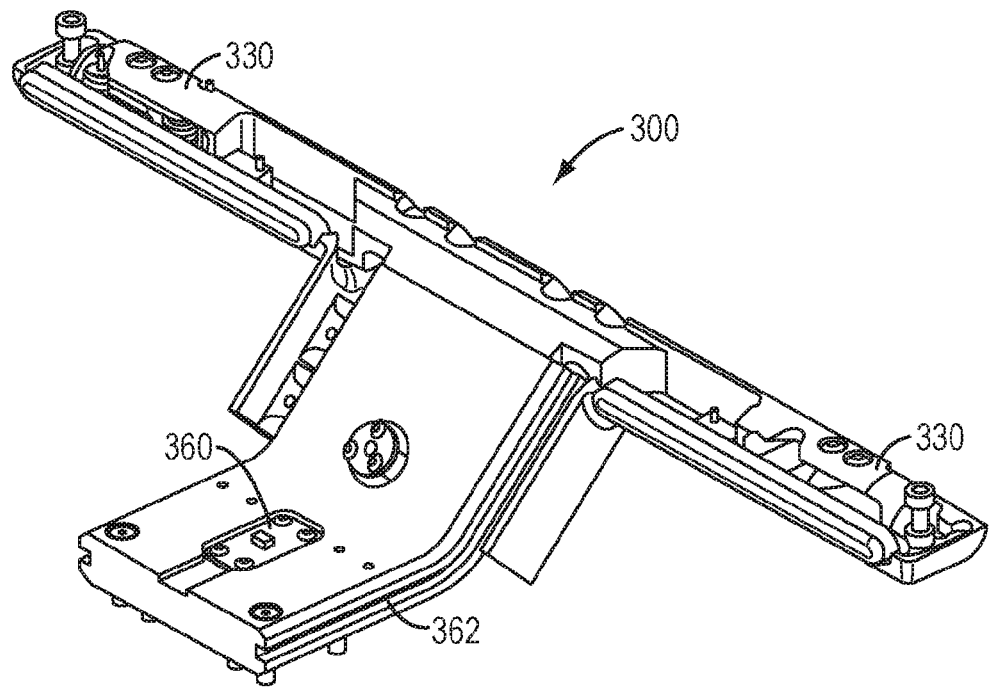
FIG. 13 is a perspective view of an exemplary embodiment of a steering interface including a calibration data storage device.

Sensors 320, 322 used in the sensor blocks 330 of a steering interface 300 may vary from one another and provide outputs that differ from one another. This may require calibration of the sensors 320, 322 relative to a controller for a drive system of a patient side cart, particularly when one steering interface is removed and replaced with another steering interface that has different sensors. To address this issue, a steering interface 300 may include a calibration device so that when the steering interface 300 is mounted to a patient side cart and the components of the steering interface 300 are connected to the controller for the drive system of the cart, the output from the sensors is automatically calibrated without additional effort from the user. For example, a steering interface 300 may include a calibration data storage device 360, as shown in the exemplary embodiment of FIG. 13.

A calibration data storage device 360 may be, for example, an electrically erasable programmable read-only memory (EEPROM) device, such as, for example, flash memory or another type of memory that stores calibration data. As will be discussed below, the calibration device 360 may be placed in signal connection with a controller of a drive system for a patient side cart when a steering interface 300 is mounted to the cart. In addition, connections for the sensor blocks 330, such as electrical lines or wires, may extend along a side portion 362 of a steering interface 300 so that connections are made between the sensors 320, 322 of the sensor blocks 330 when the steering interface 200 is mounted to the cart.

Figure 14:
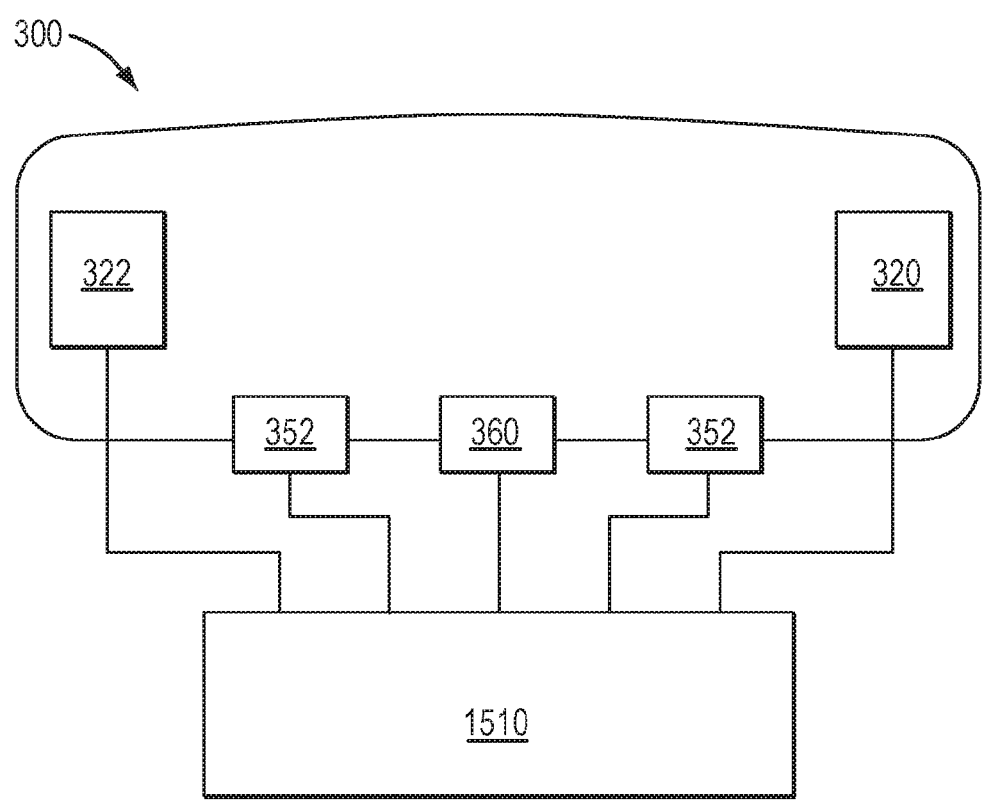
FIG. 14 is a schematic block diagram of an exemplary steering interface system connected to a patient side cart.

FIG. 14 depicts a schematic block diagram of a steering interface system in a connected state with a patient side cart, according to an exemplary embodiment. As shown in FIG. 14, when a steering interface 300 is mounted to a patient side cart 1510 (which in various exemplary embodiments can be configured like cart 110 or 210 in the exemplary embodiment of FIG. 1), sensors 220, 222 can be placed in signal connection with the cart 110, which may include a control processor for a drive system, as mentioned above. Connections may also be made between the cart and contact switches 352 in the steering interface 300 so that when a user applies a force to the trigger 350 of the steering interface 300 sufficient to engage a contact switch with a contact trigger 350, a signal may be issued from the steering interface 300 to the cart 1510, such as a signal from at least one of the contact switches 352, to indicate that a drive system of the cart 1510 should act to move the cart 1510 according to signals from sensors 320, 322. Further, a connection may be made between a calibration device 360 and the cart 1510 so that calibration data may be provided to the controller when the steering interface 300 is mounted to the cart 1510. Signals provided from the steering interface 300 to the cart 1510 may be amplified by a device of the cart 1510. In addition, cart 1510 may include an analog/digital converter to condition any signals received from the steering interface 300, as may be required.

Figure 15:
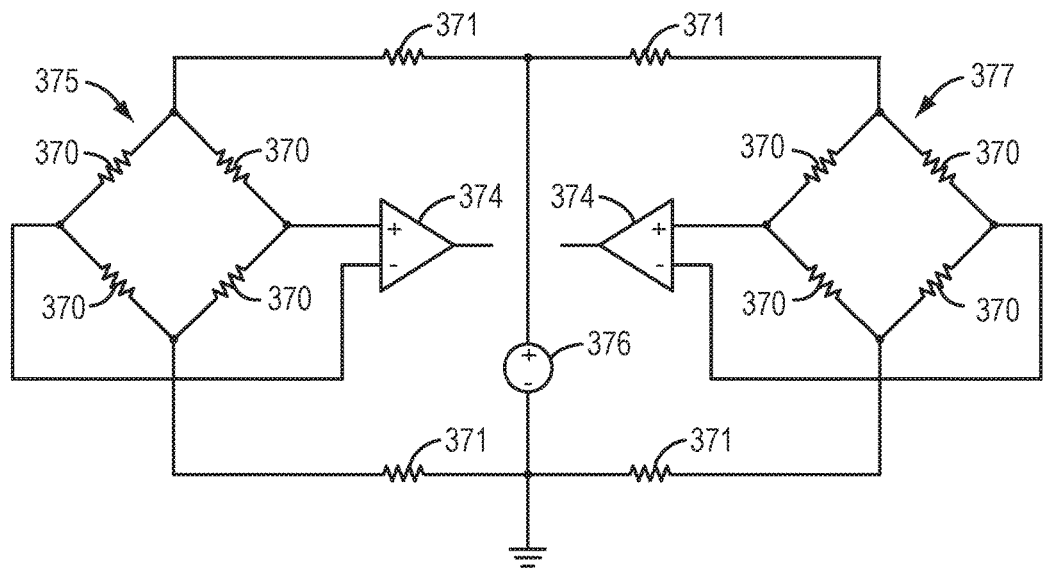
FIG. 15 is a circuit diagram including a two sensors that each include a complete Wheatstone bridge, according to an exemplary embodiment.

The sensors 320, 322 of a steering interface 300 are designed to detect a force applied by a user to the steering interface 300. As discussed above, sensors 320, 322 may be strain gauges that detect the amount of strain applied to the sensors 320, 322 and provide a corresponding signal. One design for a strain gauge includes a Wheatstone bridge. FIG. 15 depicts a circuit diagram including a first sensor 375 and a second sensor 377. Each of first sensor 374 and second sensor 377 includes a complete Wheatstone bridge, with the complete Wheatstone bridge including four sensor elements 370, according to an exemplary embodiment. The circuit further includes an amplifier 374 for each sensor and a component 376 to measure the voltage across the circuit. Numerals 371 refer to resistances due to cables and/or connectors. In the circuit shown in FIG. 15, resistances 371 due to cables and/or connectors cause relatively small errors in a sensor response. However, these errors from resistances 371 can be compensated and removed by the amplifiers 374, which may form a differential bridge amplifier.

Configurations using complete Wheatstone bridges, as shown in the exemplary embodiment of FIG. 15, result in sensors 375, 377 that each include four sensor elements 370. If a device, such as a handle in one of the exemplary embodiments discussed herein, include sensors for each of the X and Y directions at each end of the handle, the configuration results in a total of sixteen sensor elements 370 for the device. Further, if a redundant set of sensors is provided, the total number of sensor elements 370 doubles to thirty-two.

One consideration for sensors 320, 322 of a steering interface 300 is that the sensors 320, 322 are being used to measure a force applied by a person that is used by a cart drive control system to provide motion to the cart. In such an application, the sensors 320, 322 need not require the accuracy of other applications in which such sensors may be employed, such as for example making weight measurements or other sensitive force measurements. Accordingly, each sensor 320, 322 need not have that accuracy of a sensor that includes the configuration shown in FIG. 15. Instead, sensors 320, 322 may be less accurate, which advantageously permits an arrangement of the sensors that may be less costly. For instance, if strain gauges are used, sensors 320, 322 may have the configuration shown in the exemplary embodiment of FIG. 16.

Figure 16:
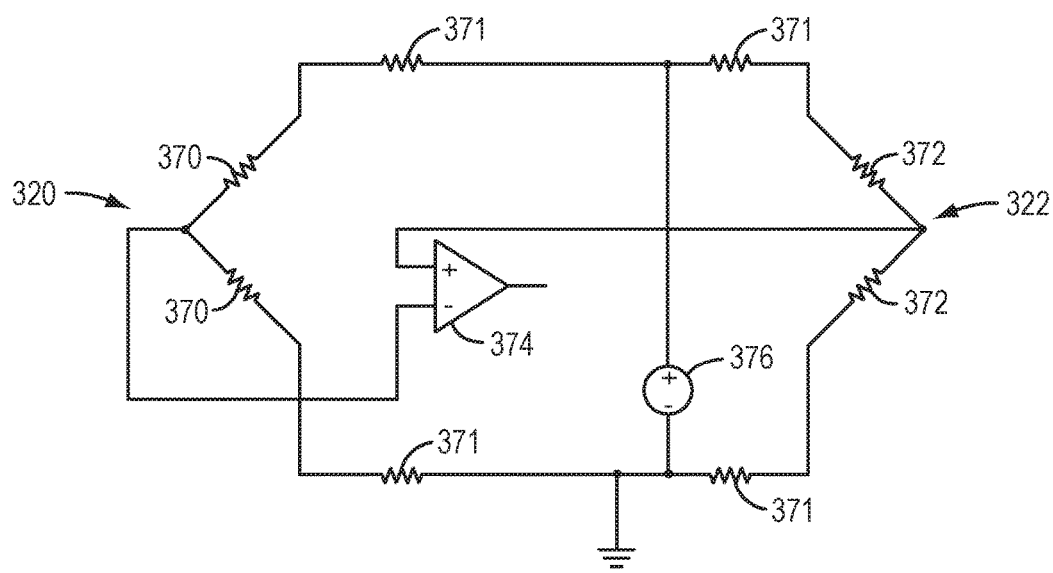
FIG. 16 is a circuit diagram including two sensors each having one half of a Wheatstone bridge, according to an exemplary embodiment.

As shown in the exemplary embodiment of FIG. 16, a Wheatstone bridge may be split so that sensor 320 includes two sensor elements 370 of the Wheatstone bridge (one half of the Wheatstone bridge) and sensor 322 includes the other two sensor elements 372 of the Wheatstone bridge (the other half of the Wheatstone bridge). The configuration shown in FIG. 16 may further include an amplifier 374 and a component 376 to measure the voltage across the circuit of FIG. 16. Thus, the total number of sensor elements 370, 372 utilized by a device, such as a handle, may be cut in half, which advantageously reduces the cost to manufacture the device. Further, an additional cost savings may be provided by using fewer amplifiers 374 because only one amplifier 374 could be used.

A potential consequence of using fewer sensor elements 370, 372 for each sensor 320, 322 is that there may be larger errors in sensor outputs. For instance, resistances 371 due to cables and/or connectors may produce errors that are not removed by the amplifier 374 shown in the exemplary embodiment of FIG. 16. Although a configuration using a split Wheatstone bridge, as shown in the exemplary embodiment of FIG. 16, may result in sensors 320, 322 that are less accurate than sensors having the configuration of FIG. 15, sensors 320, 322 may be sufficiently accurate to detect forces applied by a person to a steering interface 300. However, according to an exemplary embodiment, the accuracy of a split Wheatstone bridge may be enhanced. For instance, errors produced by a split Wheatstone bridge may be reduced by, for example, powering the bridge with four pairs of wires instead of a single pair of wires to reduce error from cable resistance, using four pairs of connector contacts instead of a single pair of connector contacts to reduce connector error, using corrosion resistant material for connectors contacts to reduce error from long term aging of the connector contact, specifying the lengths of cables for sensors 320, 322 to be substantially the same length to have substantially the same cable resistance to reduce error to due differences in cable resistance between the sensors 320, 322, and/or removing residual cable and/or connector resistance via calibration values stored in a device, such as calibration values stored in calibration data storage device 360 discussed above.

According to another embodiment, a patient side cart may include a kick plate. As shown in the exemplary embodiment of FIG. 2, a kick plate 303 having a sensor may be located at the rear of a patient side cart, e.g., the side of the cart where the steering interface is located. A steering interface 300 may be designed according to a situation when a user is pushing off of a ground surface to apply a force to the steering interface 300. However, if a user puts a foot on the back of a patient side cart in an attempt to help move the cart forward, while simultaneously holding the steering interface 300, there may be a tendency to pull back on the steering interface in the X (aft) direction. In this situation, since the force applied to the steering interface 300 is in the X (aft) direction, the cart would move backward in the aft direction toward the user, even though the user is attempting to move the cart forward by using the user's foot. To prevent this situation, the kick plate 303 can be configured to send a signal to stop power to drive the cart when a user engages or strikes the kick plate 303. According to an exemplary embodiment, kick plate 320 may disable movement of a cart if both kick plate 320 is pressed and the cart is moving in a backwards direction.

By providing a steering interface that detects forces applied by a user in a simple manner, a user may advantageously move a patient side cart that the steering interface is attached to with relative ease. For instance, the cart may include a drive system to move the relatively large weight of the patient side cart without requiring the user to provide a force necessary to move the patient side cart without assistance. In addition, the steering interface may provide a simple user interface that detects the forces applied by the user to the steering interface so that a control system may in turn determine which direction the patient side cart should be driven without requiring the user to interact with multiple, complex controls. Further, the steering interface may advantageously provide a user with a positive feel about the craftsmanship of the steering interface and the patient side cart via its solid construction and relatively smooth movements.

Exemplary embodiments, including the various operational methods described herein, can be implemented in computing hardware (computing apparatus) and/or software, such as (in a non-limiting example) any computer that can store, retrieve, process and/or output data and/or communicate with other computers. The results produced can be displayed on a display of the computing hardware. One or more programs/software comprising algorithms to affect the various responses and signal processing in accordance with various exemplary embodiments of the present disclosure can be implemented by a processor, such as data interface module, of or in conjunction with the control cart including core processor and may be recorded on computer-readable media including computer-readable recording and/or storage media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A surgical system cart comprising:
    a surgical instrument manipulator;
    a steering interface comprising a grasping surface;
    a steering sensor positioned to sense a first force exerted on the grasping surface;
    a stop sensor configured to sense a second force; and
    a drive control system operably coupled to the steering sensor and the stop sensor, wherein in an operational state, the drive control system:
        transmits drive power to move the cart in a first direction of motion in response to the steering sensor sensing the first force, and
        stops drive power to the cart in response to the stop sensor sensing the second force exerted in a direction opposite to the first direction of motion.

2. The surgical system cart of claim 1, wherein in the operational state, the drive control system stops drive power to the cart in response to the stop sensor sensing the second force while the steering sensor is sensing the first force.

3. The surgical system cart of claim 1, wherein in the operational state, the drive control system stops movement of the cart in response to the second force applied to the stop sensor while the first direction of motion is toward a user grasping the grasping surface.

4. The surgical system cart of claim 1:
    wherein the first force comprises one or more of a turning force on the cart, a forward motion force on the cart, and an aft motion force on the cart; and
    wherein the first direction of motion corresponds to the first force and comprises one or more of a turning motion of the cart, a forward motion of the cart, and an aft motion of the cart.

5. The surgical system cart of claim 1, wherein the stop sensor comprises a kick plate.

6. The surgical system cart of claim 5, wherein the steering interface and the kick plate are located on a same side of the cart.

7. The surgical system cart of claim 1, wherein the stop sensor comprises a kick plate located on the cart at a position accessible by a foot of a user grasping the grasping surface.

8. The surgical system cart of claim 7, wherein the steering interface and the kick plate are located on a same side of the cart.

9. The surgical system cart of claim 1, wherein the steering sensor is positioned to sense the first force exerted on the grasping surface by a user's hand.

10. The surgical system cart of claim 1, wherein the steering sensor comprises two or more redundant sensors.

11. The surgical system cart of claim 10, wherein the two or more redundant sensors are positioned at opposite sides of the grasping surface in positions corresponding to locations of the grasping surface for placement of a user's right and left hands during steering of the cart.

12. The surgical system cart of claim 1, wherein the steering interface is removably coupled with the cart.

13. The surgical system cart of claim 1, wherein the steering sensor comprises a strain gauge.

14. The surgical system cart of claim 1:
    wherein the cart further comprises one or more wheels; and
    wherein the drive control system is operably coupled to transmit the drive power to the or each wheel to move the cart in the first direction of motion.

15. A method of controlling movement of a surgical system cart, comprising:
    detecting a first force exerted on a grasping surface of a steering interface of the cart;
    providing drive power to move the cart in a direction of motion in response to detecting the first force;
    detecting a second force exerted on the cart in a direction generally opposite to the direction of motion of the cart; and
    ceasing the drive power to the cart in response to detecting the second force.

16. The method of claim 15, wherein the ceasing of the drive power occurs while the detecting of the first force occurs.

17. The method of claim 15:
    wherein the first force comprises one or more of a turning force on the cart, a forward motion force on the cart, and an aft motion force on the cart; and
    wherein the direction of motion corresponds to the first force and comprises one or more of a turning motion of the cart, a forward motion of the cart, and an aft motion of the cart.

18. The method of claim 15, wherein the first force is exerted on the grasping surface by a user's hand.

19. The method of claim 15, wherein the second force is exerted on a kick plate by a user's foot.

20. The method of claim 15, wherein the first force is exerted by a hand of a user and the second force is exerted by a foot of the user.

* * * * *